(12) United States Patent
Jing et al.

(10) Patent No.: US 12,105,056 B2
(45) Date of Patent: Oct. 1, 2024

(54) DEFLECTION CALIBRATION APPARATUS AND METHOD FOR LASER TYPE HIGH-SPEED DEFLECTION TESTER

(71) Applicant: RESEARCH INSTITUTE OF HIGHWAY MINISTRY OF TRANSPORT, Beijing (CN)

(72) Inventors: Genqiang Jing, Beijing (CN); Yingchao Luo, Beijing (CN); Xiaobing Li, Beijing (CN); Hongbo Guo, Beijing (CN); Qihao Yin, Beijing (CN)

(73) Assignee: RESEARCH INSTITUTE OF HIGHWAY MINISTRY OF TRANSPORT, Beijing (CN)

( * ) Notice: Subject to any disclaimer, the term of this patent is extended or adjusted under 35 U.S.C. 154(b) by 0 days.

(21) Appl. No.: 18/564,974

(22) PCT Filed: Apr. 3, 2022

(86) PCT No.: PCT/CN2022/085209
§ 371 (c)(1),
(2) Date: Nov. 28, 2023

(87) PCT Pub. No.: WO2023/151169
PCT Pub. Date: Aug. 17, 2023

(65) Prior Publication Data
US 2024/0264124 A1    Aug. 8, 2024

(30) Foreign Application Priority Data
Feb. 8, 2022  (CN) .......................... 202210117166.6

(51) Int. Cl.
*G01N 29/30* (2006.01)
*G01N 29/24* (2006.01)
*G01N 33/38* (2006.01)

(52) U.S. Cl.
CPC ......... *G01N 29/30* (2013.01); *G01N 29/2418* (2013.01); *G01N 33/383* (2013.01)

(58) Field of Classification Search
CPC .. G01N 29/30; G01N 29/2418; G01N 33/383; G01N 3/42; G01N 3/00; G01M 5/0058; G01M 5/0066; G01M 5/0091
See application file for complete search history.

(56) References Cited

U.S. PATENT DOCUMENTS

| | | |
|---|---|---|
| 5,753,808 A | 5/1998 | Johnson et al. |
| 9,261,354 B1 | 2/2016 | Mercado |

(Continued)

FOREIGN PATENT DOCUMENTS

| | | |
|---|---|---|
| CN | 102162217 A | 8/2011 |
| CN | 103643620 A | 3/2014 |

(Continued)

OTHER PUBLICATIONS

PCT/CN2022/085209—International Search Report and Written Opinion mailed on Nov. 10, 2022, 13 pages.

(Continued)

*Primary Examiner* — Suman K Nath
(74) *Attorney, Agent, or Firm* — Getech Law LLC; Jun Ye

(57) ABSTRACT

The disclosed are a deflection calibration apparatus and method for a laser type high-speed deflection tester. The apparatus comprises rigid supports, rotating discs, driving systems and a deflection calibration unit; the rotating discs are mounted on the rigid supports and driven by the driving systems to rotate, and upper surfaces of the rotating discs are processed into inclined planes having a slope in the circumferential direction; the deflection calibration unit is used for calibrating a laser type high-speed deflection tester according to measured and theoretical deflection values; laser (Continued)

emitted by a Laser-Doppler vibrometer is incident on the upper surfaces of the rotating discs to obtain the measured deflection value; the deflection calibration unit calculates the theoretical deflection value according to the inclination angle and the rotational angular velocity of each rotating disc and the distance between a laser incident point and the gyration center of each rotating disc.

12 Claims, 3 Drawing Sheets

(56) References Cited

U.S. PATENT DOCUMENTS

| | | | | |
|---|---|---|---|---|
| 2008/0304083 | A1* | 12/2008 | Farritor | B61K 9/08 356/614 |
| 2013/0283924 | A1* | 10/2013 | McCullough | G01N 3/00 250/461.1 |
| 2023/0026408 | A1* | 1/2023 | Dittmann | F21S 41/25 |

FOREIGN PATENT DOCUMENTS

| | | |
|---|---|---|
| CN | 104032657 A | 9/2014 |
| CN | 204059166 U | 12/2014 |
| CN | 107085126 A | 8/2017 |
| CN | 108333072 A | 7/2018 |
| CN | 114481769 A | 5/2022 |
| CN | 114481769 B | 11/2022 |
| JP | 2016023537 A | 2/2016 |
| WO | 2018233838 A1 | 12/2018 |

OTHER PUBLICATIONS

CN202210117166.6—First Office Action mailed on Sep. 7, 2022, 8 pages.
CN202210117166.6—Notification of Granting Patent for Invention mailed on Oct. 18, 2022, 3 pages.

* cited by examiner

DEFLECTION CALIBRATION APPARATUS AND METHOD FOR LASER TYPE HIGH-SPEED DEFLECTION TESTER

CROSS REFERENCE OF RELATED APPLICATIONS

The present application is a 371 of international Application PCT/CN2022/085209, filed Apr. 3, 2022, which claims priority to Chinese Patent Application No. 202210117166.6, filed Feb. 8, 2022. The contents of the applications are incorporated herein by reference in their entireties.

FIELD

The present application relates to the field of laser calibration, and particularly relates to a deflection calibration apparatus and method for a laser type high-speed deflection tester.

BACKGROUND OF THE INVENTION

In recent decades, pavement detection and evaluation techniques have been developed very rapidly, and conventional static or go-stop measurement methods such as the Beckman beam method and the drop hammer method have failed to meet the development demands of modern society. A Laser type high-speed deflection tester is the most advanced dynamic deflection testing apparatus in the world at present. The apparatus measures a descent speed $v_m$ of the pavement under load using Laser-Doppler technique during high-speed travel, and performs inversion to obtain a maximum deflection value do and a deflection basin d(x) of the pavement based on an Euler-Bernoulli beam model and a two-parameter model for a deflection basin or an area method, with a detection speed of 100 km/h, which has the advantages of low detection cost, high safety, and can reflect real-time conditions of the pavement in time.

Although various conventional methods, such as the Beckman beam method and the drop hammer method, are currently available for detecting pavement deflection, and corresponding test procedures and calibration specifications have been formed, such procedures or specifications are not suitable for use in the laser type high-speed deflection tester, mainly due to different load-loading modes of test equipment, different principles for deflection measurement and calculation, and the like. Although numerous experiments have shown that the measurement results based on the laser type high-speed deflection tester have good reproducibility and are highly correlated with the results of the conventional measurement methods, the widespread use of new techniques in the engineering field is still affected due to the realistic conditions of inability to perform metrological calibration and provenance.

SUMMARY OF THE INVENTION

In view of this, the present application provides a deflection calibration apparatus and method for a laser type high-speed deflection tester to calibrate a laser type high-speed deflection tester.

According to an aspect of the present application, the present application provides a deflection calibration apparatus for a laser type high-speed deflection tester, including rigid supports, rotating discs, driving systems, and a deflection calibration unit.

The rotating discs are mounted on the rigid supports, and are driven to rotate by the driving systems, and upper surfaces of the rotating discs are machined to be inclined planes having slopes in a circumferential direction.

The deflection calibration unit is configured to calibrate the laser type high-speed deflection tester according to a measured deflection value and a theoretical deflection value.

Laser emitted by Laser-Doppler vibrometers in the laser type high-speed deflection tester is incident to the upper surfaces of the rotary rotating discs to obtain the measured deflection value.

The deflection calibration unit calculates the theoretical deflection value according to an inclination angle of each rotating disc, a rotational angular velocity, and a distance between a laser incident point and a gyration center of each rotating disc.

Preferably, the apparatus is provided with a plurality of rotating discs arranged in sequence and corresponding driving systems, wherein a quantity of the rotating discs is not less than that of the Laser-Doppler vibrometers in the laser type high-speed deflection tester.

Preferably, the slope of the upper surface of each rotating disc in the circumferential direction simulates a slope of one point on a pavement deflection basin, the slopes of the upper surfaces of the plurality of rotating discs in the circumferential direction are different from each other to simulate the pavement deflection basin.

Preferably, vibration measurement points on the rotating discs have linear speeds in the circumferential direction for simulating a driving speed, and have linear speeds in a laser direction for simulating a pavement deflection speed.

The driving system include motors and drivers, wherein the motors and the rotating discs are coaxially mounted on the rigid supports.

Preferably, the rigid supports are provided with beams to which the motors are fixed.

Preferably, upper parts of the rigid supports are provided with through holes through which laser is incident to the rotating discs.

Preferably, the motors are fixedly connected to the rigid supports or the beams via flanges.

Preferably, lower sides of the motors are suspended, and/or the rotating discs have no direct contact with the rigid supports.

Preferably, the deflection calibration unit calculates the theoretical deflection value based on an Euler-Bernoulli beam theory and a two-parameter model for a deflection basin according to the slopes of the upper surfaces of the rotating discs and rotational speeds of the motors.

The present application provides a deflection calibration method for a laser type high-speed deflection tester, including:

allowing laser emitted by Laser-Doppler vibrometers in a laser type high-speed deflection tester to be incident to upper surfaces of rotary rotating discs to obtain a measured deflection value; machining the upper surfaces of the rotating discs to be inclined planes having slopes in a circumferential direction;

calculating a theoretical deflection value according to an inclination angle of each rotating disc, a rotational angular velocity, and a distance between a laser incident point and a gyration center of each rotating disc; and calibrating the laser type high-speed deflection tester according to the measured deflection value and the theoretical deflection value.

Preferably, calculating the theoretical deflection value includes:

calculating the theoretical deflection value based on an Euler-Bernoulli beam theory and a two-parameter model for a deflection basin according to the slopes of the upper surfaces of the rotating discs and rotational speeds of motors.

The present application provides the technical solution of calibration for the laser type high-speed deflection tester based on discrete and relative movement concepts. Non-destructive calibration of the measurement results of the laser type high-speed deflection tester is achieved by simulating the slopes of different measurement points on the deflection basin, and performing inversion to obtain the pavement deflection basin and deflection standard values based on the slopes of a plurality of measurement points, which breaks through the current inability of measurement and calibration of the laser type high-speed deflection tester.

Other features and advantages of the present application will be described in detail in the following specific embodiments.

BRIEF DESCRIPTION OF DRAWINGS

The drawings, which form a part of the present application, are used to provide further understanding of the present application, and illustrative embodiments of the present application and the description thereof serve to explain the present application. In the drawings.

DETAILED DESCRIPTION OF THE INVENTION

It should be noted that the embodiments and the features in the individual embodiments in the present application can be combined with each other without conflict.

The present application will now be described in detail in combination with the embodiments with reference to the drawings.

Major difficulties in designing and researching a laser type high-speed deflection calibration apparatus includes: accurate simulation of a deflection speed $v_m$ on the premise of guaranteeing a vehicle speed $v_k$; and provenance of a defection value $d_0$ and a deflection basin $d(x)$.

Figure 1:
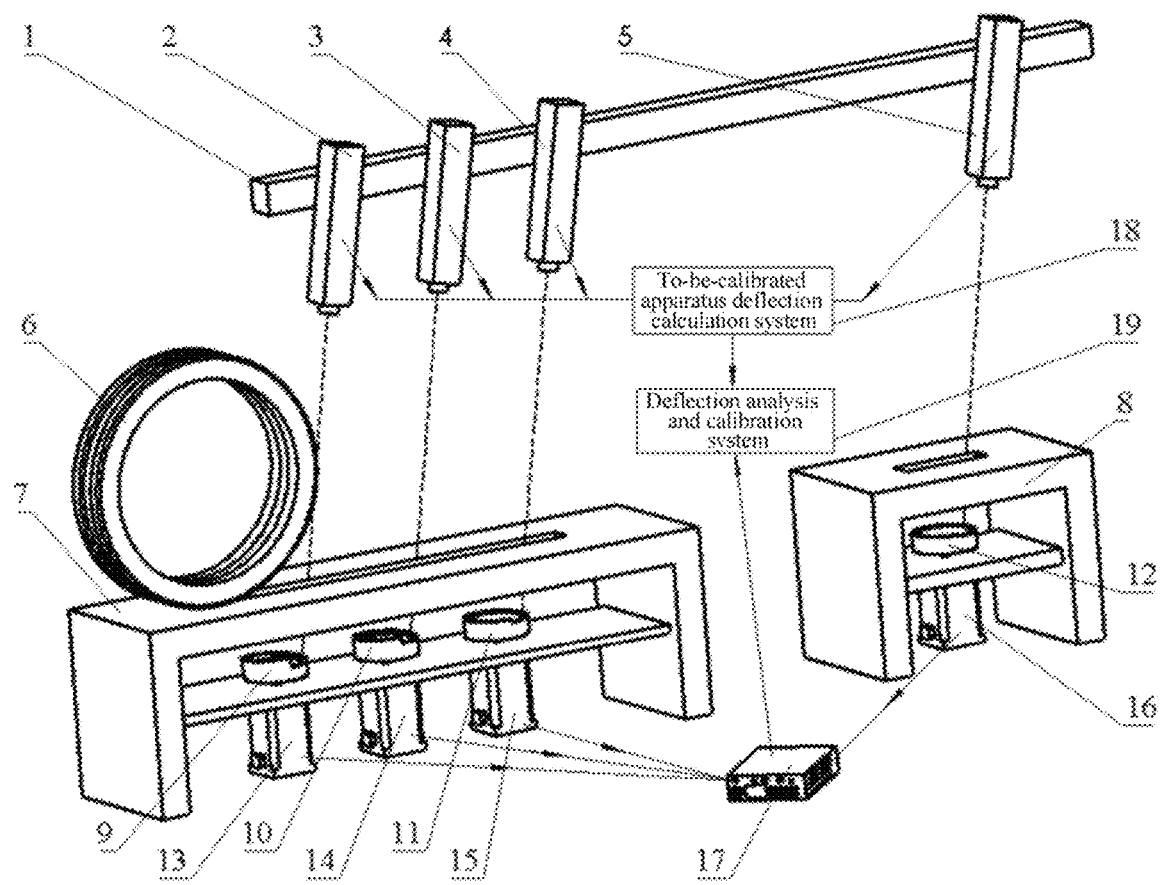
FIG. 1 is a calibration apparatus for a laser type high-speed deflection tester provided by the present application.

In order to achieve the function of laser type high-speed deflection calibration, the present application provides a calibration apparatus for a laser type high-speed deflection tester, which is as shown in FIG. 1. The calibration apparatus for the laser type high-speed deflection tester includes: a rigid support 7, a rigid support 8, a rotating disc 9, a rotating disc 10, a rotating disc 11, a rotating disc 12, a driving motor 13, a driving motor 14, a driving motor 15, a driving motor 16, a driver 17, and a deflection analysis and calibration system 19. The rigid supports mainly play the roles of supporting a to-be-tested apparatus, separating rear axle tires from the ground, and mounting the driving motors.

A beam 1, a Laser-Doppler vibrometer 2, a Laser-Doppler vibrometer 3, a Laser-Doppler vibrometer 4, a Laser-Doppler vibrometer 5, a tire 5 and a to-be-calibrated apparatus deflection calculation system 18 are apparatus or components possessed by a to-be-calibrated laser type high-speed deflection tester.

Rotating discs simulate the relative movement of a laser type high-speed pavement deflection tester and the pavement. There are a plurality of rotating discs, and the quantity of the rotating discs depends on the quantity of Laser-Doppler vibrometers of the laser type high-speed deflection tester. Upper surfaces of the rotating discs are machined to be inclined planes having slopes in a circumferential direction, which are used to simulate deflection slopes at different positions of a deflection basin. During test, a plurality of rotating discs with different slopes are arranged below the laser type high-speed pavement deflection tester in sequence, and it needs to be ensured that a measuring point for each Laser-Doppler vibrometer of the to-be-calibrated apparatus can measure a vibration speed at a certain point on the inclined plane of each rotating disc. Different pavement deflection basins can be simulated by adjusting the slopes of the inclined planes of the rotating discs.

Driving systems include driving motors, drivers, etc. The driving motors are coaxially connected to the rotating discs, and drive the rotating discs to perform circumferential movement, and the rotational speed can be adjusted by the drivers. Since the inclined planes are machined on the rotating discs, a laser measurement point on the rotating disc may displace due to rotation of the rotating disc to simulate the deflection speed at this location. Points having the same radius on the rotating disc have the same linear speed for simulating a driving speed. Different driving speeds can be simulated by adjusting the rotational speeds of the driving motors.

The present application relates to a plurality of Laser-Doppler vibrometers (2, 3, 4, 5), rigid supports (7, 8), rotating discs (9, 10, 11, 12), and driving motors (13, 14, 15, 16). As shown in FIG. 1, by taking the Laser-Doppler vibrometer 2, the rigid support 7, the rotating disc 9, and the driving motor 13 as an example, other Laser-Doppler vibrometers, rigid supports, rotating discs, and driving motors may refer to FIG. 1 in terms of connection manner, mounting location and relative relationship, and may operate in the same or similar manner.

The rotating disc 9 and the driving motor 13 are coaxially mounted, and the driving motor 13 is fixedly connected to the rigid support 7 by a flange. A lower side of the driving motor 13 is suspended. The rotating disc 9 has no direct contact with the rigid support 7. A through hole is cut in the middle of the upper surface of the rigid support 7 such that laser emitted from the Laser-Doppler vibrometer 2 passes through the through hole and irradiates the upper surface of the rotating disc 9. The driving motor 13 is connected to the driver 17 by a signal line. A beam is mounted in the middle of the rigid support, which facilitates the mounting of the driving motor. It should be noted that it is a feasible solution that the driving motor is directly mounted on the top of the rigid support without the beam.

Figure 2:
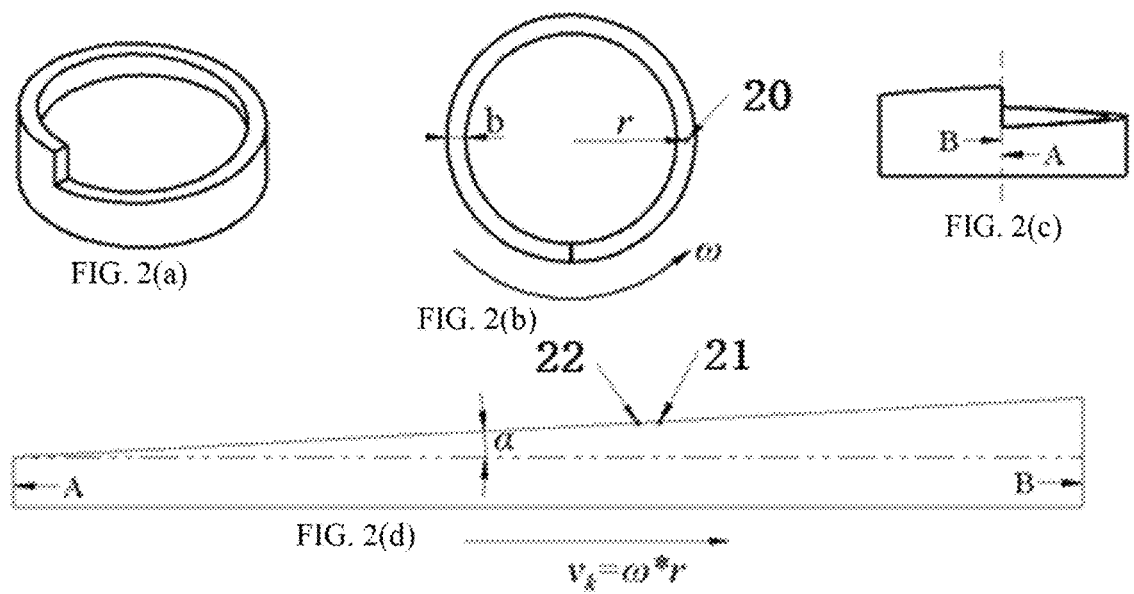
FIG. 2(a)-FIG. 2(d) are isometric side view, top view, front view and circumferentially extended view of a rotating disc provided by the present application.

An isometric side view, top view, front view and circumferentially extended view of the rotating disc 9 are shown in FIGS. 2(a)-2(d). An upper side of the rotating disc 9 is machined to be an inclined plane with an inclination angle α and a width b. Laser emitted by the Laser-Doppler vibrometer 2 passes through the through hole of the rigid support 7 to irradiate an incident point 20 on the inclined plane, and the center of a light spot of a laser incident point is spaced from a gyration center of the rotating disc 9 by a horizontal linear distance r. The distance r can be controlled by the size of the rotating disc 9. FIG. 2(d) shows a laser incident point 21 at a moment t and a laser incident point 22 at a moment t+Δt.

When the to-be-calibrated laser type high-speed deflection tester is calibrated, a driver is required to stop a vehicle on the calibration apparatus, for example, the tire 6 is pressed against the rigid support 7. The deformation of the entire calibration apparatus under the action of the tire 6 can be neglected due to the greater rigidity of the rigid support 7.

It is known that the rotating disc 9 is driven by the drive motor 13 to perform a counterclockwise circumferential movement with an angular speed ω, the circumferential linear speed at the incident point simulates the driving speed $v_k$, where $v_x=\omega*r$.

The laser incident point originating from the Laser-Doppler vibrometer 2, i.e., a first laser measurement point, will move along the inclined plane at the upper side of the rotating disc 9 according to the principle of relative movement when the rotating disc 9 performs circumferential movement with the angular speed ω. Since the direction of rotation is counterclockwise, pavement descent is simulated in this process, wherein the descent speed of deflection is $v_m$. Assuming that descent displacement of the laser measurement point is $\Delta y=v_m*\Delta t$, and relative displacement of the laser measurement point in a circumferential direction is $\Delta x=v_k*\Delta t$ within time $\Delta t$, $\Delta y/\Delta x=v_m/v_k$. The inclined plane with the inclination angle α at the upper side of the rotating disc 9 decides a slope k of a deflection basin at this location, wherein $k=\tan(\alpha)$. It can be known from the geometrical relationship that the slope is $k=\Delta y/\Delta x$, and the descent speed of deflection simulated by the rotating disc 9 is $v_m = \tan(\alpha)*v_k=\tan(\alpha)*\omega*r$.

It can be known from the above analysis that the descent speed $v_m$ of deflection corresponding to any point on the deflection basin can be simulated by controlling the rotational angular velocity @ of the rotating disc 9, the inclination angle α of the inclined plane at the upper side of the rotating disc 9 in the circumferential direction, and the distance r from the laser measurement point to the gyration center of the rotating disc 9.

A descent speed $v_{mi,1}$ of deflection of an ith deflection basin corresponding to the first laser measurement point can be simulated by changing an inclination angle $\alpha_{i,1}$ of the inclined plane at the upper side of the rotating disc 9, wherein $v_{mi,1}=\tan(\alpha_{i,1})*\omega*r$, i=1, 2, 3 . . . , N. Similarly, a descent speed $v_{mi,j}$ of the ith deflection basin corresponding to a jth laser measurement point can be simulated by changing an inclination angle $\alpha_{i,j}$ of the inclined plane of each of the rotating discs 10, 11, 12, wherein $v_{mi,j}=\tan(\alpha_{i,j})*\omega*r$, and J represents a jth Laser-Doppler vibrometer.

The evaluation on the pavement deflection by the to-be-calibrated laser type high-speed deflection tester relies on the deflection speeds $v_{mi,j}$ measured by the Laser-Doppler vibrometers (2, 3, 4, 5), and the relationship of the measured deflection value $d_{0,I}$ and deflection speed $v_{mi,j}$ of the pavement can be expressed using an equation (1):

$$d_{0,i}=f_i(v_{mi,j},x_j,v_k), i=1,2,3, \ldots ; j=1,2,3, \ldots ,N \quad (1)$$

wherein, in the equation, x; represents a horizontal distance from the jth Laser-Doppler vibrometer of the to-be-calibrated laser type high-speed deflection tester to the centers of axial loads of rear axles, and $v_k$ represents a driving speed of a vehicle. It should be noted that in practical application, the measurement speed $v'_{mi,j}$ of the Laser-Doppler vibrometer is not equivalent to the deflection speed $v_{mi,j}$ of the pavement, and there is a certain numerical relationship between the measurement speed and the deflection speed. In the present application, the measurement speed and the deflection speed are equivalent in order for illustration.

In the present application, the deflection speed $v_{mi,j}$ of the pavement is converted into the rotational speed w of the rotating disc, the inclination angle $\alpha_{i,j}$ of the inclined plane, and the distance r, and then the pavement deflection $D_{0,I}$ simulated by the calibration apparatus can be expressed using an equation (2):

$$D_{0,i}=F(\alpha_{i,j},x_j,\omega,r), i=1,2,3, \ldots ; j=1,2,3, \ldots ,N \quad (2)$$

For the deflection calibration experiment for the laser type high-speed deflection tester under certain conditions, a to-be-simulated driving speed $v_k$ is determined, i.e., ω*r is a constant value. If a driving speed $v_k$=72 km/h is determined, the distance r=100 mm and the angular speed ω=200 rad/s of the rotating disc may be taken. Finally, the pavement deflection $D_{0,i}$ simulated by the calibration apparatus is only related to the inclination angle $\alpha_{i,j}$ of the inclined plane.

The deflection analysis and calibration system 19 is a deflection calibration unit that first calculates a theoretical deflection value of the calibration apparatus based on an Euler-Bernoulli beam theory and a two-parameter model for a deflection basin according to the slopes of the upper surfaces of the rotating discs (9, 10, 11, 12) and the rotational speeds of the driving motor (13, 14, 15, 16), and second calibrates the measurement result of the to-be-calibrated apparatus according to the measured deflection value and the theoretical deflection value of the to-be-calibrated apparatus.

Figure 3:
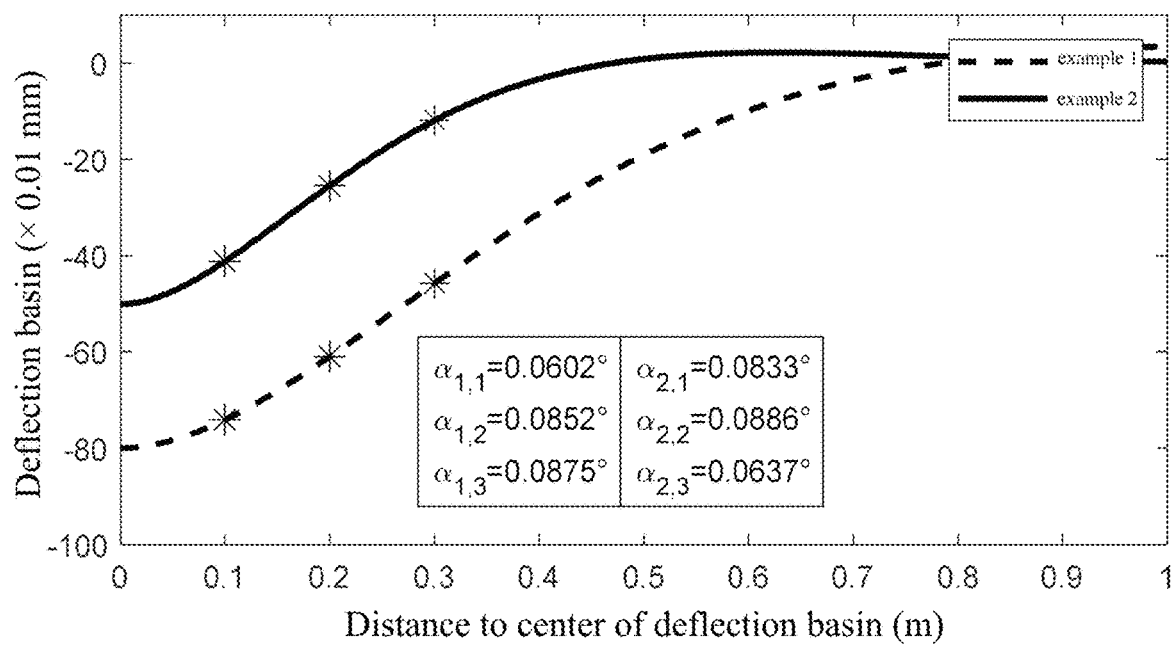
FIG. 3 is an example of two deflection basin curves provided by the present application.

FIG. 3 describes two deflection basin curves which are corresponding to two pavement types respectively, wherein $\alpha_{i,j}$ represents an inclination angle of a jth rotating disc for an ith deflection basin, wherein i=1, 2, 3 . . . , j=1, 2, 3, . . . , N. The two curves can serve as deflection basin curves for provenance, pavement deflections $D_0$ at the centers of axle loads are equal to −0.80 mm and −0.50 mm respectively, which can be taken as deflection values aiming at provenance. It is assumed that the to-be-calibrated laser type high-speed deflection tester is provided with four Laser-Doppler vibrometer, and distances $x_j$ from the mounting locations to the centers of the axle loads are 0.1 m, 0.2 m, 0.3 m and 3.6 m, respectively. Since the Laser-Doppler vibrometer 5, which is farthest from the center of the axle load (x=3.6 m), is at the farthest end of the deflection basin during operation, and is often used as a reference and angle calibration in practical application, it can be considered that deflection $d_{3600}$, a deflection slope $Slope_{3600}$ and an inclination angle $\alpha_{i,4}$ at this location are all 0. Slopes and inclination angles $\alpha_{i,j}$ at other three locations are as shown in the figure. Four slopes, inclination angles $\alpha_{i,j}$, distances r and rotational speeds ω of the rotating discs are input into the deflection analysis and calibration system 19, an thus, deflection speeds $v_{mi,j}$ at four measurement points of four Laser-Doppler vibrometers can be simulated. A corresponding deflection speed curve can be fitted based on the speeds $v_{mi,j}$ and a two-parameter equation for a to-be-simulated deflection basin.

Figure 4:
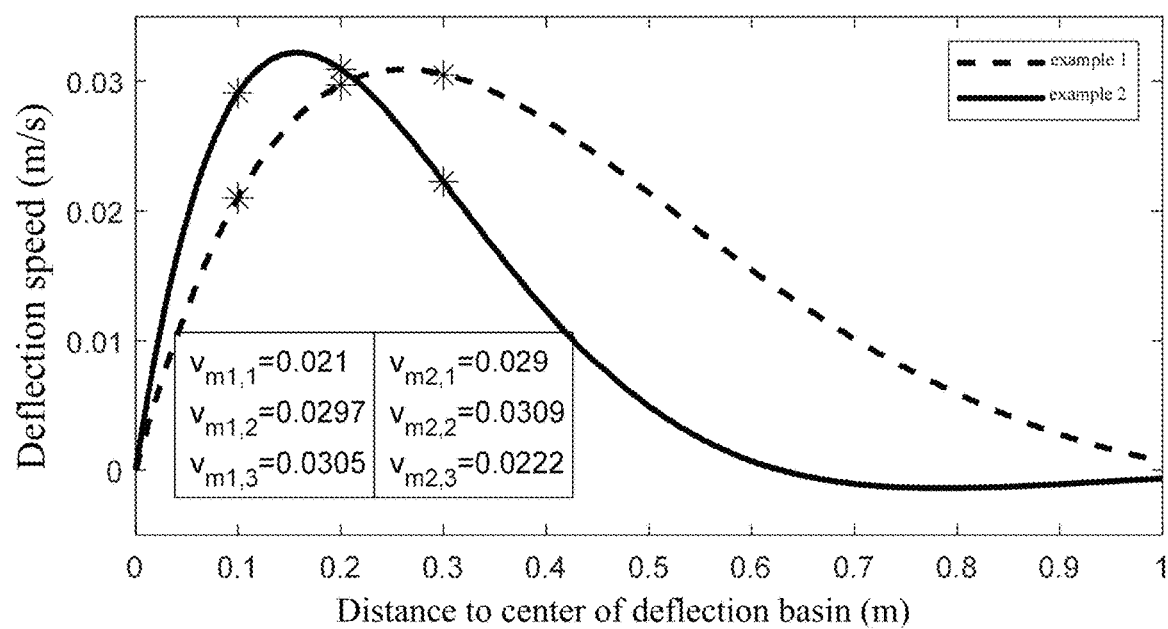
FIG. 4 is an example of two deflection basin speed curves provided by the present application.

The two-parameter equation d(x) for the deflection basin is as shown in an equation (3), wherein two parameters are A and B, respectively. A deflection speed $v_m(x)$ corresponding to the two-parameter equation is as shown in FIG. 4. A maximum deflection $d_0$ corresponding to the two-parameter equation is as shown in an equation (5).

$$\overline{y}(x) = -\frac{A}{2B}e^{-Bx}(\cos(Bx) + \sin(Bx)) \quad (3)$$

$$\dot{\overline{y}}_\perp(x) = Ae^{-Bx}(\sin(Bx))v_k \quad (4)$$

$$\overline{y}_{d_o} = -\frac{A}{2B} \quad (5)$$

FIG. 4 shows two deflection basin speed curves obtained by fitting, wherein $v_{mi,j}$ represents a deflection speed simulated by a jth rotating disc for an ith deflection basin, wherein i=1, 2, 3 ..., j=1, 2, 3, ..., N. In the fitting process, the two parameters of the two-parameter equation are: A=0.0048, B=3 and A=0.005, B=5 respectively, and maximum deflections do corresponding to the speed curves are 0.0008 m and 0.0005 m, respectively.

It can be known that the simulated deflection value is consistent with the theoretical deflection value by comparing the theoretical deflection value $D_0$ in FIG. 3 with the simulated deflection value $d_0$ inverted in FIG. 4, which shows the correctness of the calibration apparatus for simulation of deflection and the deflection inversion method.

The simulation and deflection provenance of a certain pavement deflection basin are achieved in the above process.

A plurality of types of pavement deflection basins can be simulated by changing the inclination angles $\alpha_{i,j}$ of the rotating discs, that is, simulating the pavement deflection by the calibration apparatus has higher versatility.

After the Laser-Doppler vibrometers (2, 3, 4, 5) of the to-be-calibrated laser type high-speed deflection tester measure the deflection speeds simulated by the plurality of rotating discs (9, 10, 11, 12) of the calibration apparatus, the to-be-calibrated apparatus deflection calculation system 18 outputs corresponding deflection values, and then the measured deflection values are input into the deflection analysis and calibration system.

The inclination angles $\alpha_{i,j}$ of a plurality of sets of rotating discs are set to simulate a plurality of types of pavement deflection basins so that the calibration apparatus and the to-be-calibrated apparatus can simultaneously calculate the theoretical deflection value and measured deflection value. An indication error of the to-be-calibrated apparatus can be evaluated by comparing a standard deflection value with the measured deflection value, thereby calculating a correction value or a calibration factor.

The deflection calibration work of the laser type high-speed deflection tester is implemented in the above process.

The present application further provides a deflection calibration method for the laser type high-speed deflection tester, including:
allowing laser emitted by laser-Doppler vibrometers in a laser type high-speed deflection tester to be incident to upper surfaces of rotary rotating discs to obtain a measured deflection value; machining the upper surfaces of the rotating discs to be inclined planes having slopes in a circumferential direction;
calculating a theoretical deflection value according to an inclination angle of each rotating disc, a rotational angular velocity, and a distance between a laser incident point and a gyration center of each rotating disc; specifically, calculating the theoretical deflection value based on an Euler-Bernoulli beam theory and a two-parameter model of a deflection basin according to the slopes of the upper surfaces of the rotating discs and rotational speeds of motors; and
calibrating the laser type high-speed deflection tester according to the measured deflection value and the theoretical deflection value.

It can be known from the above analysis and the equation (2) that the calibration apparatus can satisfy simulation and provenance of different pavement deflections. The calibration method is suitable for deflection calibration tests of different laser type high-speed deflection testers at different driving speeds $v_k$, for examples, there may be different quantities N of Laser-Doppler vibrometers, and different mounting locations $x_j$(j=1, 2, 3, ..., N) of the Laser-Doppler vibrometers.

The calibration apparatus for the laser type high-speed deflection tester simulates and reflects the deflection forming mechanism of the laser type high-speed deflection tester based on the discrete and relative movement concepts, which achieves calibration of the measured deflection value of such apparatus.

The above descriptions are merely preferred embodiments of the present application and are not intended to limit the present application. Any modification, equivalent replacement, improvement, and the like made to within the spirit and principle of the present application all fall within the scope of protection of present application.

What is claimed:

1. A deflection calibration apparatus for a laser type high-speed deflection tester, comprising rigid supports, rotating discs, driving systems, and a deflection calibration unit, wherein
   the rotating discs are mounted on the rigid supports, and are driven to rotate by the driving systems, and upper surfaces of the rotating discs are machined to be inclined planes having slopes in a circumferential direction;
   the deflection calibration unit is configured to calibrate the laser type high-speed deflection tester according to a measured deflection value and a theoretical deflection value;
   laser emitted by Laser-Doppler vibrometers in the laser type high-speed deflection tester is incident to the upper surfaces of the rotating discs to obtain the measured deflection value; and
   the deflection calibration unit calculates the theoretical deflection value according to an inclination angle of each rotating disc, a rotational angular velocity, and a distance between a laser incident point and a gyration center of each rotating disc.

2. The deflection calibration apparatus according to claim 1, comprising the rotating discs arranged in sequence and corresponding driving systems, wherein a quantity of the rotating discs is not less than that of the Laser-Doppler vibrometers in the laser type high-speed deflection tester.

3. The deflection calibration apparatus according to claim 2, wherein the slope of the upper surface of each rotating disc in the circumferential direction simulates a slope of one point on a pavement deflection basin, the slopes of the upper surfaces of the rotating discs in the circumferential direction are different from each other to simulate the pavement deflection basin.

4. The deflection calibration apparatus according to claim 1, wherein vibration measurement points on the rotating discs have linear speeds in the circumferential direction for simulating a driving speed, and have linear speeds in a laser direction for simulating a pavement deflection speed.

5. The deflection calibration apparatus according to claim 1, wherein the driving systems comprise motors and drivers, and the motors and the rotating discs are coaxially mounted on the rigid supports.

6. The deflection calibration apparatus according to claim 5, wherein the rigid supports are provided with beams to which the motors are fixed.

7. The deflection calibration apparatus according to claim 5, wherein upper parts of the rigid supports are provided with through holes through which laser is incident to the rotating discs.

8. The deflection calibration apparatus according to claim 5, wherein the motors are fixedly connected to the rigid supports or the beams via flanges.

9. The deflection calibration apparatus according to claim 5, wherein lower sides of the motors are suspended, and/or the rotating discs have no direct contact with the rigid supports.

10. The deflection calibration apparatus according to claim 5, wherein the deflection calibration unit calculates the theoretical deflection value based on an Euler-Bernoulli beam theory and a two-parameter model for a deflection basin according to the slopes of the upper surfaces of the rotating discs and rotational speeds of the motors.

11. A deflection calibration method for a laser type high-speed deflection tester according to the deflection calibration apparatus for the laser type high-speed deflection tester of claim 1, comprising:

allowing laser emitted by Laser-Doppler vibrometers in a laser type high-speed deflection tester to be incident to upper surfaces of the rotating discs to obtain a measured deflection value; machining the upper surfaces of the rotating discs to be inclined planes having slopes in a circumferential direction;

calculating a theoretical deflection value according to an inclination angle of each rotating disc, a rotational angular velocity, and a distance between a laser incident point and a gyration center of each rotating disc; and calibrating the laser type high-speed deflection tester according to the measured deflection value and the theoretical deflection value.

12. The deflection calibration method according to claim 11, wherein calculating the theoretical deflection value comprises:

calculating the theoretical deflection value based on an Euler-Bernoulli beam theory and a two-parameter model for a deflection basin according to the slopes of the upper surfaces of the rotating discs and rotational speeds of motors.

* * * * *